US006576193B1

(12) United States Patent
Cui et al.

(10) Patent No.: US 6,576,193 B1
(45) Date of Patent: Jun. 10, 2003

(54) DEVICE AND METHOD FOR COLLECTING AND TESTING FLUID SPECIMENS

(76) Inventors: Shujie Cui, 3619 Syracuse Ave., San Diego, CA (US) 92122; Alice H. Yu, 3619 Syracuse Ave., San Diego, CA (US) 92122

( * ) Notice: Subject to any disclaimer, the term of this patent is extended or adjusted under 35 U.S.C. 154(b) by 391 days.

(21) Appl. No.: 09/698,630

(22) Filed: Oct. 27, 2000

(51) Int. Cl.[7] ............................................. G01N 21/01
(52) U.S. Cl. ........................ 422/58; 422/55; 422/68.1; 422/82.05; 422/102; 436/164; 436/165; 436/169; 436/807; 73/864; 73/864.32; 73/864.63; 73/864.91; 73/864.34
(58) Field of Search ........................... 422/55, 58, 68.1, 422/82.05, 102; 436/164, 165, 169, 807; 73/864, 864.32, 864.34, 864.63, 864.91

(56) References Cited

U.S. PATENT DOCUMENTS

| | | | |
|---|---|---|---|
| 3,552,213 A | * | 1/1971 | Auchapt et al. .......... 73/864.34 |
| 4,797,256 A | * | 1/1989 | Watlington, IV ............. 422/58 |
| 4,827,944 A | | 5/1989 | Nugent |
| 4,976,923 A | | 12/1990 | Lipsky et al. |
| 5,022,411 A | | 6/1991 | Guirguis |
| 5,119,830 A | | 6/1992 | Davis |
| 5,215,102 A | | 6/1993 | Guirguis |
| 5,352,410 A | * | 10/1994 | Hansen et al. ................ 422/58 |
| 5,403,551 A | | 4/1995 | Galloway et al. |
| 5,429,804 A | | 7/1995 | Sayles |
| 5,501,837 A | | 3/1996 | Sayles |
| 5,569,225 A | | 10/1996 | Fleury |
| 5,595,187 A | | 1/1997 | Davis |
| 5,603,903 A | | 2/1997 | Copelan |
| 5,656,502 A | | 8/1997 | MacKay et al. |
| 5,882,600 A | | 3/1999 | Davis |
| 5,897,840 A | | 4/1999 | Owens, Jr. et al. |
| 5,976,895 A | | 11/1999 | Cipkowski |
| 6,054,099 A | | 4/2000 | Levy |
| 6,063,341 A | | 5/2000 | Fassbind et al. |
| 6,074,606 A | | 6/2000 | Sayles |
| 6,277,646 B1 | * | 8/2001 | Guirguis et al. ............ 436/165 |

FOREIGN PATENT DOCUMENTS

WO    WO 99/56630    11/1999

* cited by examiner

Primary Examiner—Jill Warden
Assistant Examiner—LaToya I. Cross
(74) Attorney, Agent, or Firm—Foley & Lardner

(57) ABSTRACT

Devices and methods for collecting a fluid specimen and testing it are disclosed that avoid unduly exposing the tester to the specimen and eliminate the possibility of contaminating the remaining portion of the collected fluid. The device includes a first compartment for collecting the fluid and provides controlled volumes of fluid from the first compartment to a second compartment where the fluid is accessible to test strips. Fluid from the first compartment is transferred to the second compartment by use of a fluid metering valve having a valve cylinder with one or more wells formed on the surface of the cylinder. The fluid metering valve is fluidly connected to the first compartment at a first valve position and is fluidly connected to the second compartment at a second valve position.

26 Claims, 4 Drawing Sheets

US 6,576,193 B1

DEVICE AND METHOD FOR COLLECTING AND TESTING FLUID SPECIMENS

FIELD OF THE INVENTION

The present invention relates generally to fluid specimen containers and analytical testing methods for analyzing the contents of fluid specimens and, more specifically, to fluid specimen containers designed to transfer fluid to test strips or other containers for testing purposes.

BACKGROUND OF THE INVENTION

Analysis of body fluids such as urine or blood typically involves a first step of collecting the fluid sample in a container and then removing a sample of the fluid from the container to analyze it in the desired test format. For example, the fluid is removed from the container using a pipette and is then applied to a chemical or immunoassay test strip. A serious problem with this approach is that the tester may become exposed to the bodily fluid during the removal or pipetting procedure and may become infected with agents contained in the fluid.

A variety of fluid collection devices have been devised to limit tester exposure by combining the test component with the container (see, e.g. U.S. Pat. Nos. 4,827,944; 4,976,923; 5,119,830; 5,595,187; 5,501,837; 5,429,804; and 6,974,606). These devices, however, have various design limitations. For example, in some designs, testing occurs immediately rather than when actually desired. In other designs, the tests are built into the lid of the container, requiring inversion of the device to enable the specimen to exit the storage compartment and contact the test component. Inverting the device, however, raises the possibility for accidental leakage and makes it difficult to control the volume of fluid that is released to the test strip. Such designs also have the potential to contaminate the main fluid compartment with test reagents that flow backward from the testing compartment.

Thus, a need exists for improved specimen fluid collection devices that provide controlled volumes of fluid to the test strips when desired, eliminate contamination by back flow, and avoid unduly exposing the tester to the liquid specimen.

SUMMARY OF THE INVENTION

The present invention is directed to solving the problem alluded to above. Briefly, the device comprises: (a) a first compartment for receiving a fluid specimen to be tested and including a cover lid for fluidly sealing the first compartment; (b) a fluid metering valve comprising an assembly bearing and a valve cylinder disposed therein and rotatable along its longitudinal axis, said cylinder having one or more wells formed on the surface of the cylinder, said wells in fluid connection with said first compartment when said valve is at a first valve position; and (c) a second compartment in fluid connection to said wells of said valve cylinder when said valve is at a second valve position, said second compartment designed to receive one or more reagent test strips for testing the specimen fluid.

Also provided are a variety of valve cylinder well designs, including use of multiple wells, variations in well positioning, variations in well dimensions and combinations of the above.

In another embodiment, the device comprises at least one additional fluid metering valve in fluid connection with the first compartment when said additional valve is in a first position and is in fluid connection with at least one additional second compartment when the additional valve is at a second valve position.

In other embodiments, fluid connection between the valve cylinder and the first or second compartment can be achieved by means of a passageway.

In yet another embodiment, the fluid metering valve is located within a support structure. The second compartment also may be formed within the support structure.

In other embodiments, access to the second compartment is controlled by a protective cover.

The device also may comprise: (a) a first compartment for receiving a fluid specimen to be tested and including means for fluidly sealing the first compartment; (b) a second compartment designed to receive one or more reagent test strips for testing the fluid specimen; (c) a fluid metering valve comprising a valve cylinder disposed therein and rotatable along its longitudinal axis, said cylinder having one or more wells formed on the surface; and (d) means for fluidly connecting the fluid metering valve to said first compartment at a first valve cylinder position and to said second compartment at a second valve position.

This device includes additional embodiments similar to those described above.

Also provided herein is a method for using the device to collect and test a fluid specimen. The method comprises using one or more reagent test strips that avoids exposing the tester to the collected fluid and contaminating the collected fluid with the test strips, the method comprising the steps of: (a) collecting a fluid specimen into the first compartment of the device of the present invention; (b) rotating the cylinder of the fluid metering valve of the device to a first valve position so that the one or more wells connected to the first compartment each fill with a volume of the fluid specimen suitable to perform the testing; (c) rotating the cylinder of the fluid metering valve following step (b) to the second valve position so that the one or more wells are connected to the second compartment; and (d) inserting the one or more test strips into said second compartment so that each test strip contacts a suitable volume of fluid accessible to the second compartment and thereby initiating the test, wherein a fluid specimen is tested using one or more reagent test strips.

In another embodiment, the method is used to measure the presence or amount of an analyte by immunoassay while in another embodiment, the fluid tested is urine.

These and still other embodiments are discussed in more detail below.

BRIEF DESCRIPTION OF THE DRAWINGS

The various features and advantages of the present invention will become more clearly appreciated as a detailed description of the preferred embodiment is given with reference to the appended drawings.

FIG. 3A shows a valve cylinder having multiple wells and multiple separate passageways connecting to separate troughs at the bottom of the second compartment. FIG. 3B shows a valve cylinder having a single longitudinal well aligning with a single passageway connecting to the second compartment.

In FIG. 4, two fluid metering valves are shown, each directly connecting to a separate passageway which connects to a separate second compartment.

In FIG. 5, a single fluid metering valve is shown directly connecting with separate passageways each connecting to a separate second compartment.

In FIG. 6, the fluid metering valve is located below the bottom of the first compartment and the valve is connected directly to the passageway.

In FIG. 7, the passageway is eliminated, providing direct access of the test card or test strip to the wells of the valve cylinder through the second compartment.

In FIG. 8, the second compartment is configured in a different relation to the first compartment and the fluid metering cylinder is connected directly to the passageway.

In FIG. 9, the device includes an integral protective cover for the second compartment and a cap for the cover.

DETAILED DESCRIPTION OF THE INVENTION

Provided herein is a fluid specimen collecting and testing device and methods for using same. The device is suitable for collecting and testing any fluids, however, the fact that the tester is not appreciably exposed to the collected fluid makes the device particularly suited for the collection and testing of animal body fluids, particularly body fluids from a human. Any body fluid can be collected for testing with the device including, for example, urine, whole blood, blood serum or blood plasma. It will be readily apparent to those skilled in the art that the disclosed device and methods are suitable for testing of other fluid samples such as river water, pool water, ocean water and the like.

It also will be understood that one can test a body solid (e.g. stool) or any other solid with the device provided the body solid undergoes processing to generate a fluid specimen. Methods to solubilize or extract a soluble fraction from a solid specimen such as by use of detergents, denaturants or other agents are well known in the art. The body solid is preferably collected and processed to generate a fluid specimen before the fluid specimen is added to the collection and testing device.

Figure 1:
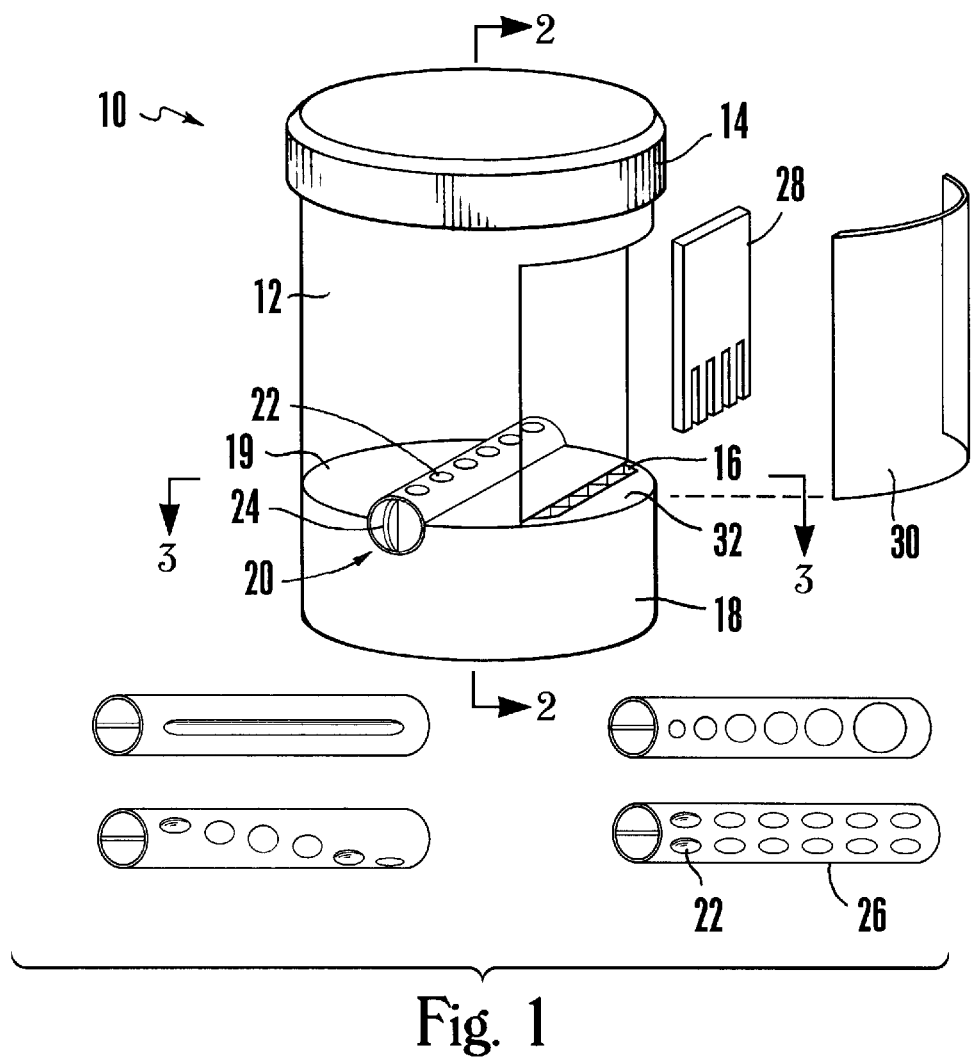
FIG. 1 is a perspective side view of a sketch of the fluid collecting and testing device with lid, first chamber for collecting fluid, fluid metering valve, test card and removable protective cover. Valve cylinders of the fluid metering valve also are shown with variation in well arrangements and dimensions.

A preferred embodiment of the present fluid collecting and testing device 10 is shown in FIG. 1. It comprises a first compartment 12 for collecting and storing fluid to be tested and a lid 14 for sealing the fluid within the first compartment. The lid may be fluidly sealed to the top of the first compartment by methods well known in the art including, for example, use of matching screw threads on the outside top of the first compartment and the inside lip of the lid. FIG. 1 also shows an opening to a second compartment 16 formed outside of first compartment 12 and in support structure 18, which also forms the base 19 of first compartment 12. Fluid metering valve 20 with wells formed thereon 22 is shown partially contained within support structure 18.

Valve 20 has a short narrow extension 24 at one end which is accessible to the outside of the device and is used to rotate the valve. The extension may extend from the device or be within a recessed area in the body of the cylinder. All that is required is to provide a means for the user to be able to turn the cylinder. Below the collecting device depicted in FIG. 1 are various embodiments of valve cylinders 26. The valve cylinders varying in well arrangements and well dimensions. As indicated in the figure, a cylinder can have one or more rows of wells, each row of a similar dimension and forming a single line along the longitudinal axis of the cylinder. Separate rows may be situated at opposite positions on the cylinder surface (i.e., 180° from each other) or may be situated closer together. In addition, a cylinder may have more than two rows of wells.

Rows on a cylinder may vary in dimension from round to elongated in shape and in the volume of liquid that they hold. A cylinder also may have a row of wells where each well has a different dimension. The wells of a cylinder also need not be spaced in a single line. By spacing at different positions, fluid is delivered from each well to the second compartment at different valve position. A well also can be in the form of a trough that extends along the longitudinal axis of the cylinder. Clearly, one of ordinary skill can readily envision a variety of cylinder designs with combinations of wells and rows not shown in FIG. 1. The number of wells in a row of the cylinder also can vary.

The fluid collection and testing device of the invention can be manufactured and sold with a single fluid metering valve installed in position and for ready use. Alternatively, or in addition, the device can be manufactured with the ability to remove and replace valve cylinders. In this case, the user may be provided with a selection of valve cylinders that are compatible with the device and can mount the cylinder of choice into the device before use.

As shown in FIG. 1, the opening to second compartment 16 is designed to receive test unit 28 for testing fluid in the second compartment. Optional cover 30 can be applied to cover recessed area 32 of compartment 16 to protect the test unit when the device is used for testing.

Figure 2:
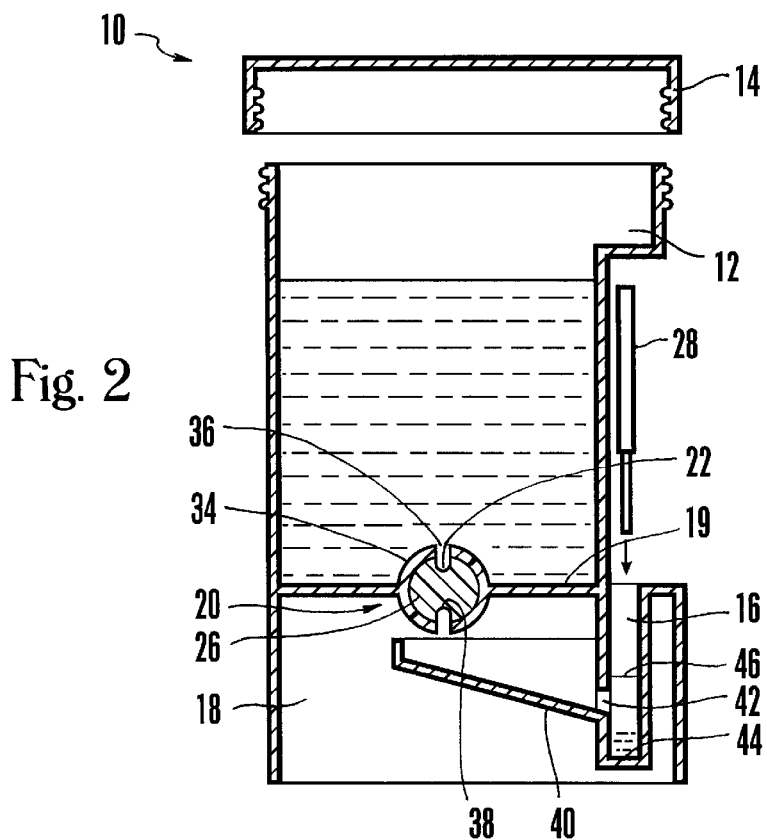
FIG. 2 is a vertical sectional view substantially along the line 2—2 in FIG. 1, showing interior details of the fluid collecting and testing device including the first compartment, fluid metering valve, second compartment and a passageway providing a connection for fluid between the valve and the second compartment.

FIG. 2 is a vertical sectional view of the device showing the fluid metering valve 20 partly within support structure 18 including rotatable valve cylinder 26 seated within bearing assembly 34. The portion of the bearing assembly 34 that is contained within support structure 18 can be integral to the support structure or can be made as a separate component. Valve cylinder 26 is shown with wells 22 formed as a depression on the surface of the cylinder, but not extending all the way through the diameter of the cylinder. The wells 22 of cylinder 26 take up a fixed volume of fluid from the first compartment 12 when the wells are in fluid connection with the first compartment. Fluid connection is accomplished as shown in FIG. 2 by positioning the valve cylinder at a first position where the cylinder well 22 is aligned with opening 36 in bearing assembly 34. Bearing opening 36 may be a single longitudinal opening that provides access to all the wells of a cylinder row at the same time. Alternatively, there may be multiple bearing openings in the bearing, each opening aligning with and providing fluid access with a well of the cylinder.

Once fluid from compartment 12 passes through the valve assembly opening 36 and fills wells 22, the fluid metering valve is rotated to a second position where well (shown as 38) is in fluid connection with the second compartment 16. Fluid connection occurs when fluid leaves well 38 and flows via passageway 40 through second compartment access hole 42 (positioned as a low point in the compartment relative to the cylinder to allow the fluid leaving the well 38 to flow by gravity to compartment 16). Fluid entering second compartment 16 collects at the bottom of compartment 44.

Figures 3A, 3B:
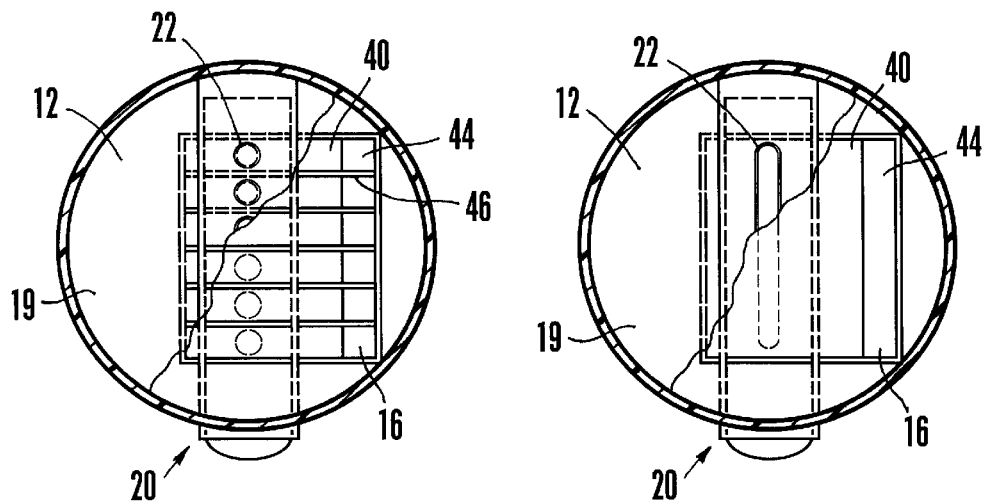
FIGS. 3A and 3B are horizontal sectional views taken substantially along the line 3—3 in FIG. 1. The relationship of the fluid metering valve to the passageway linking to the second compartment is shown.

FIGS. 3A and 3B are horizontal sectional views of the fluid testing device looking down through the opening of the first compartment. The relationship of the fluid metering valve 20 to passageway 40 linking to second compartment 16 is shown. FIG. 3A shows a valve cylinder having multiple wells 22, multiple passageways 40 connecting to separate troughs 46 at the bottom 44 of the second compartment 16. The separation into troughs 46 at the bottom 44 of second compartment 16 is spaced to allow receipt of separate test devices such as separate test strips mounted on a single test card. The number of troughs normally should match the number of wells in a single row of the valve cylinder.

FIG. 3B shows a valve cylinder having a single longitudinal well 22 aligning with a single passageway 40 connecting to the bottom of second compartment 16. Thus, in this case, there is a single well and a single trough at the bottom of the second compartment.

The purpose of the first compartment is for fluid collection and retention. The purpose of the second compartment 16 varies with the embodiment. In some embodiments, the second compartment 16 serves to provide access for a test strip or test card to reach the fluid at the bottom of the second compartment which has collected there following distribution through the fluid metering valve 20. In other embodiments, the second compartment serves to provide access for a test strip or test card to reach fluid within the wells of the cylinder. In yet another embodiment, the second compartment 16 serves to hold fluid collecting containers.

Figure 4:
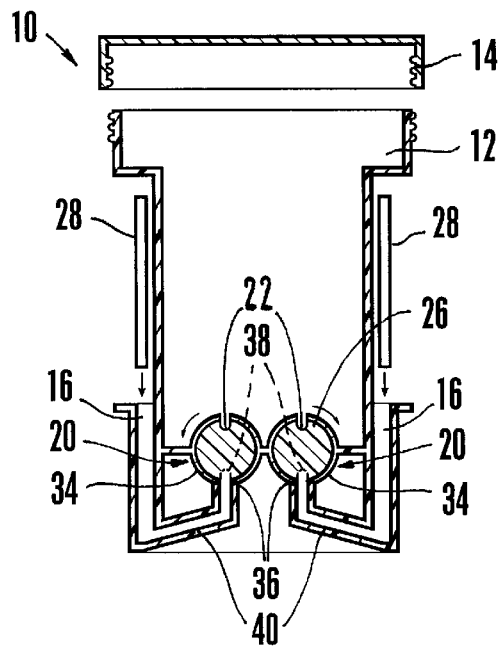
FIG. 4 is a vertical sectional view of the fluid collecting and testing device similar to that shown in FIG. 2.

FIG. 4 depicts an embodiment having a single first chamber 12 and two separate fluid metering valves 20, each connecting to a separate second chamber 16. In this case, fluid connection occurs when the metering valve is in a second valve position. At this point, fluid in wells 38, passing through opening 36 of bearing 34, flows via a separate passageway 40 to collect in a separate second compartment 16. Thus, the same device can be used to run two assay tests at the same time.

Figure 5:
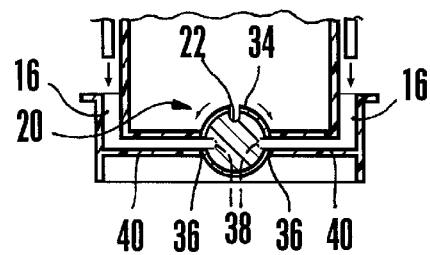
FIG. 5 is a vertical sectional view of the fluid collecting and testing device similar to that shown in FIG. 2.

FIG. 5 shows an alternative embodiment where a single first chamber 12 connects to two second chambers 16 by a single fluid metering valve 20. Passageway 40 in FIG. 5, although shown nearly level to bearing opening 36, still must direct fluid on a downhill path to second compartment 16 in order to take advantage of gravity. One skilled in the art can readily appreciate additional embodiments involving one or more fluid transfer valves in conjunction with one or more second compartments.

Figure 6:
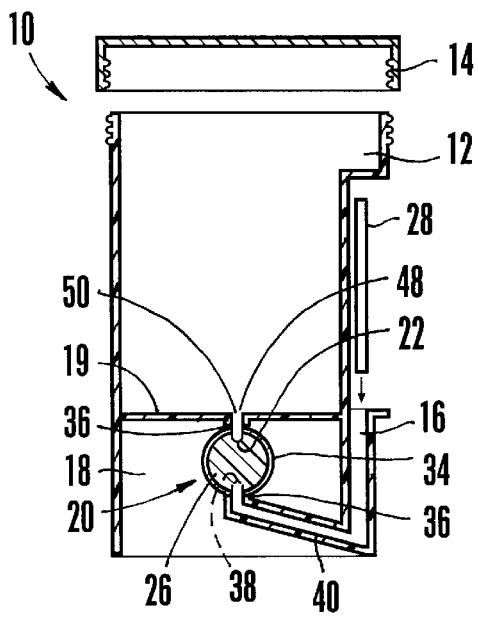
FIG. 6 is a vertical sectional view showing interior details of the fluid collecting and testing device similar to that shown in FIG. 2.

FIG. 6 is a vertical sectional view of an embodiment of the invention where fluid metering valve 20 is positioned fully within the support structure 18. In this case, an opening 48 is provided in bottom 19 of first compartment 12. Opening 48 connects to passageway 50 in the support structure, which connects to opening 36 in valve bearing 34. Thus, when the fluid metering valve is in a first valve position, the well 22 of cylinder 26 aligns with the opening 36 in valve bearing 34, thus placing the well of the metering valve in fluid connection with the first chamber. There may be a separate opening 48 connecting to a separate passageway 50 for each opening 36 in the valve bearing 34. Alternatively, opening 48 may be a single long trough-shaped opening connecting via a single passageway 50 to each opening in the valve bearing. Clearly different arrangements are possible depending on the valve cylinder well arrangement chosen.

Figure 7:
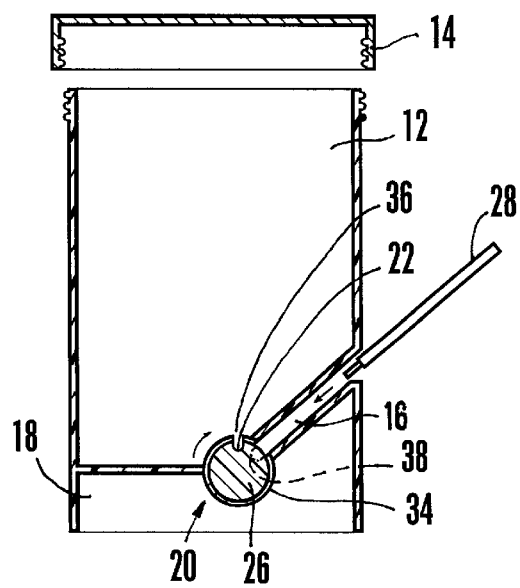
FIG. 7 is a vertical sectional view of the fluid collecting and testing device that is similar to FIG. 2.

FIG. 7 is a vertical sectional view of an embodiment of the invention where the second compartment 16 is directly connected to the wells 22 of fluid metering valve 20, thus providing fluid connection without the use of a passageway. In this design, when the valve is in a first position, fluid from the first chamber 12 passes through opening 36 in valve bearing 34 to fill well 22. When the metering valve is rotated to a second valve position, fluid connection is provided to the second chamber 16. At this point, test device 28 can be inserted into the second chamber 16 and directly contact fluid within the wells 38 of cylinder 26.

Figure 8:
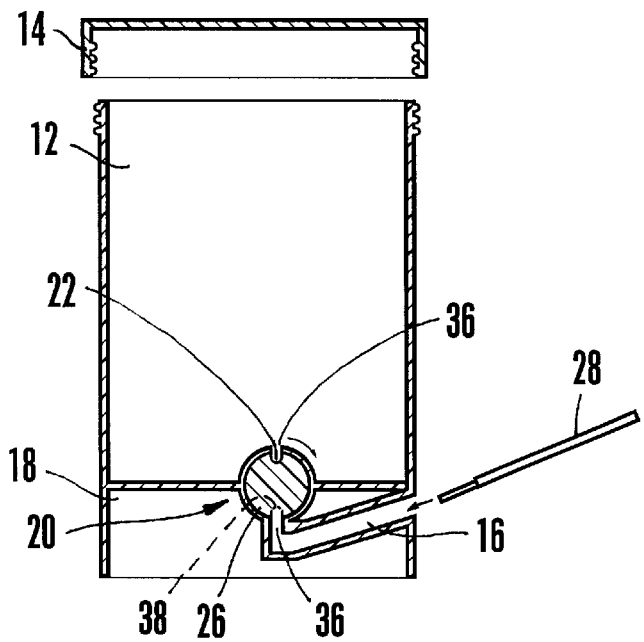
FIG. 8 is a side view of the fluid collecting and testing device that is similar to FIG. 2.

FIG. 8 is a side view of an embodiment of the invention showing second compartment 16 positioned nearly horizontal with respect to its position in FIG. 2, where it is shown in an essentially vertical position. It is appreciated that second compartment 16 may be located anywhere between a vertical position and a horizontal position provided that at the second metering valve position, fluid exists the wells and flows to bottom of 16 where it is retained.

The second compartment 16 also can have any number of sizes and shapes For example, the second compartment 16 can be designed with contours that follow the shape of test card 28. The second compartment also may be much larger than the shape of a test card. In this latter embodiment, the device can be configured such that the second compartment is below the first compartment and the test card 28 can be placed horizontally within the second compartment 16 below the cylinder so as to receive fluid that is released from wells of the cylinder. Alternatively, in this design, the second compartment 16 can hold one or more fluid containers such as a tube or a plate with wells, positioned to receive the fluid released from the valve cylinder wells. The fluid container or plate with wells can be removed from the device and tested elsewhere.

Figure 9:
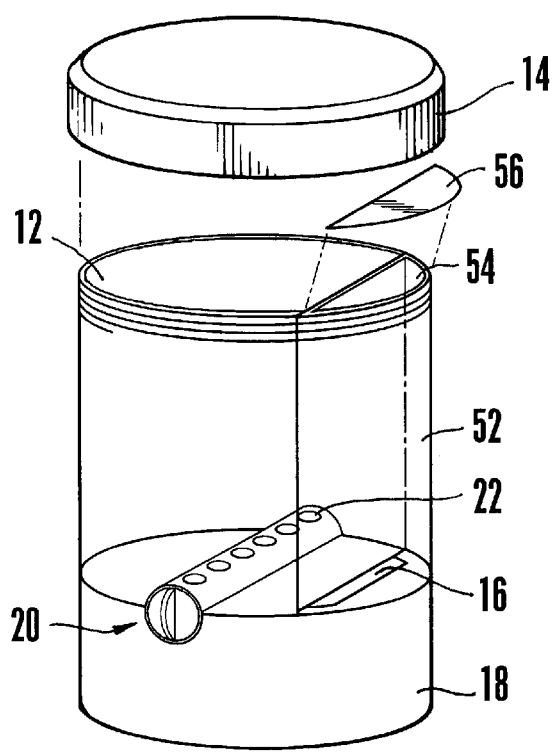
FIG. 9 is a perspective view showing a fluid collection and testing device similar to FIG. 1.

FIG. 9 is a perspective view showing an alternative embodiment of the protective cover design shown in FIG. 1. In this case, opening to second chamber 16 is enclosed within a protective compartment 52 having an opening at top 54 and a cover 56. Thus, when using this device, lid 14 and cover 56 are removed, test unit (not shown: e.g. test strip or test card) can be inserted through opening 54 and into second compartment 16.

Generally the fluid collecting and testing device 10, can be sterilized as a whole or can be separated into a lid and fluid container which are separately sterilized and packaged. Preferably the entire device with the lid attached is sterilized and stored in a sterile package.

The present invention provides methods to collect and test a fluid specimen using one or more reagent test strips in conjunction with the collecting and testing device disclosed herein. Body fluid to be tested can be collected from any animal, preferably from a human by standard methods. In the case of human body fluids, the donor may collect his/her own urine specimen while the assistance of a professional should generally be used if blood is collected. If an anti-coagulant agent is used to collect the blood, plasma is obtained following centrifugation and pelleting of blood cells. If no anti-coagulant is used, the blood is allowed to clot and the serum is separated from the clot using standard methods such as centrifugation. Blood plasma or serum thus obtained can be added to the first compartment 12 of the device 10 with our without dilution. Alternatively, whole blood collected with anti-coagulants may be added to the first compartment 12 of the collecting and testing device 10 and tested using test strips or test cards designed for use with whole blood (see, e.g., U.S. Pat. No. 6,036,919).

In the case of human urine, the fluid donor can remove the testing device lid 14 and discharge urine into the first compartment 12. Afterwards, the lid 14 is affixed in fluid-tight relationship thereon such as by screw threads or other attachment means. The collected fluid can now be tested or may be stored in the device for later testing. The simplicity of the device and the ease of using reagent test unit (e.g. test strip or test card) allows testing to be conducted in the office or in the laboratory.

To initiate testing, in general, the fluid metering valve is rotated to a first position where wells are in fluid connection with fluid in the first compartment. A tab 24 at the end of the cylinder 26 (see FIG. 1) assists the operator in rotating the valve cylinder within its seat assembly 34 (see FIG. 2). Once the wells are filled, the cylinder, of the metering valve is rotated to a second valve position where the filled wells are in fluid alignment a second compartment 16 via passageway 40 (see FIG. 2).

As shown in many of the figures, a test unit is positioned in the second compartment so that each test contacts a suitable volume of fluid at the bottom of the compartment to properly initiate and complete the test. A test unit is typically a single test strip or a card containing multiple test strips affixed.

Test strips using immunoassay technology to detect the presence of a particular analyte in the fluid can be used individually or attached to a card or solid backing made, for example, from cardboard or plastic as is well known in the art. Immunoassay test strips can be of any format including direct binding, competition as well as double or single antibody assays. Individual test strips and cards with multiple test strips attached can be prepared by methods well known in the art (see, e.g. Carlberg, IVD Technology, vol. 5(no.3), p46, May/June 1999, U.S. Pat. Nos. 5,141,850, 5,976,895, 5,770,458, and 6,036,919). Test strips whereby analyte detection involves visualization of colloidal gold or colored particles such as latex are preferred.

The test strip or card with test strips also can contain one or more chemical patches, each of which changes to a degree of color indicative of a characteristic of the test fluid. For example, in the case of pH testing, one of the patches will change to a particular color, or shade of color, depending upon a pH level of the test fluid. Chemical test patches for measuring pH, protein, glucose, ketone, bilirubin, blood and urobilinogen among others are well known in the art. A test card also can contain a mixture of test strips including immunoassay test strips as well as test strips with chemical patches.

When the test unit is properly inserted into the second compartment, the bottom end of the test strip contacts fluid at the lower end of the second compartment. The fluid is drawn along the reagent test strip until it comes to bands of the chromatographic immunoassay test reagent where a color change can occur to perform the desired test. One can visualize the test results while the test strips are positioned in the second compartment or the test card may be removed from the device after contacting the fluid and be read at a later time.

The invention thus has been disclosed broadly and illustrated in reference to representative embodiments described above. Those skilled in the art will recognize that various modifications can be made to the present invention without departing from the spirit and scope thereof. All publications; patent applications and issued patents, are herein incorporated by reference to the same extent as if each individual publication, patent application or issued patent were specifically and individually indicated to be incorporated by reference in its entirety.

What is claimed is:

1. A device for specimen fluid collection and for testing the fluid with reagent test strips, said device comprising:
    (a) a first compartment for receiving a fluid specimen to be tested and including a cover lid for fluidly sealing the first compartment;
    (b) a fluid metering valve comprising an assembly bearing and valve cylinder disposed therein and rotatable along its longitudinal axis, said cylinder having one or more wells formed on the surface, said wells in fluid connection with said first compartment when said valve cylinder is at a first valve position; and
    (c) a second compartment in fluid connection to said wells of said valve cylinder when said valve is at a second valve position, said second compartment designed to receive one or more reagent test strips for testing the fluid specimen one or more test strips disposed within the second compartment.

2. The device of claim 1 wherein said cylinder of said fluid metering valve contains multiple wells.

3. The device of claim 2 wherein said multiple wells of said cylinder form a single line running parallel with the longitudinal axis of the cylinder such that all of the wells will fill with fluid and discharge the fluid at a single valve position.

4. The device of claim 3 wherein said cylinder of said fluid metering valve contains more than a single line of wells.

5. The device of claim 2 wherein said multiple wells of said cylinder are spaced out of alignment with each other such that each of the wells will fill with fluid and discharge fluid at a different valve position from the other wells.

6. The device of claim 2 where said multiple wells of said cylinder differ in the volume of fluid that can be contained in the well.

7. The device of claim 2 wherein said well of said cylinder is formed in the shape of a trough running along the longitudinal axis of the cylinder.

8. The device of claim 1 wherein said device further comprises at least one additional fluid metering valve in fluid connection with said first compartment when said additional cylinder valve is in a first position and in fluid connection with at least one additional second compartment when said additional valve cylinder is at a second valve position, wherein said additional second compartments are each designed to receive one or more reagent test strips for testing the fluid.

9. The device of claim 1 wherein said first compartment is located above said second compartment.

10. The device of claim 1 wherein said wells of said valve cylinder at a second valve position and said second compartment are in fluid connection by means of a passageway.

11. The device of claim 1 wherein said wells of said valve cylinder at a first valve position and said first compartment are in fluid connection by means of a passageway.

12. The device of claim 1 wherein wells of said valve cylinder at a second valve position are directly accessible to the one or more reagent test strips inserted into the second compartment.

13. The device of claim 1 wherein said fluid metering valve is located within a support structure.

14. The device of claim 13 wherein said second compartment is formed within said support structure.

15. The device of claim 1 wherein access to the second compartment is controlled by a protective cover.

16. A device for specimen fluid collection and for testing the fluid with reagent test strips, said device comprising:

(a) a first compartment for receiving a fluid specimen to be tested and including means for fluidly sealing the first compartment;

(b) a second compartment designed to receive one or more reagent test strips for testing the fluid specimen;

(c) a fluid metering valve comprising a valve cylinder disposed therein and rotatable along its longitudinal axis, said cylinder having one or more wells formed on the surface; and (d) means for fluidly connecting the fluid metering valve to said first compartment at a first valve cylinder position and to said second compartment at a second valve position one or more test strips disposed within the second compartment.

17. The device of claim 16 wherein said means for fluidly connecting includes an assembly bearing within which the valve cylinder is disposed.

18. The device of claim 16 wherein said wells of said valve cylinder at a first valve position and said second compartment are fluidly connected by means of a passageway.

19. The device of claim 16 wherein said wells of said valve cylinder at a first valve position and said first compartment are in fluidly connected by means of a passageway.

20. The device of claim 16 wherein said cylinder of said fluid metering valve contains multiple wells.

21. The device of claim 20 wherein said multiple wells of said cylinder differ in the volume of fluid that can be contained in the well.

22. The device of claim 16 wherein said device further comprises at least one additional fluid metering valve in fluid connection with said first compartment when said additional cylinder valve is in a first position and in fluid connection with at least one additional second compartment when said additional valve cylinder is at a second valve position, wherein said additional second compartments are each designed to receive one or more reagent test strips for testing the fluid.

23. The device of claim 16 wherein wells of said valve cylinder at a second valve position are directly accessible to the one or more reagent test strips inserted into the second compartment.

24. A method for collecting and testing a fluid specimen using one or more reagent test strips that avoids exposing the tester to the collected fluid and contaminating the collected fluid with the test strips, the method comprising the steps of:

(a) collecting a fluid specimen into the first compartment of the device of claim 1;

(b) rotating the cylinder of the fluid metering valve of the device to a first valve position so that the one or more wells connected to the first compartment each fill with a volume of the fluid specimen suitable to perform the testing;

(c) rotating the cylinder of the fluid metering valve following step (b) to the second valve position so that the one or more wells are connected to the second compartment; and (d) inserting the one or more test strips into said second compartment so that each test strip contacts a suitable volume of fluid accessible to the second compartment and thereby initiating the test, wherein a fluid specimen is tested using one or more reagent test strips.

25. The method of claim 24 wherein said one or more test strips measures the presence or amount of an analyte by immunoassay.

26. The method of claim 24 wherein said fluid is urine.

* * * * *